US009517024B2

(12) United States Patent
Kiani et al.

(10) Patent No.: US 9,517,024 B2
(45) Date of Patent: Dec. 13, 2016

(54) OPTICAL-BASED PHYSIOLOGICAL MONITORING SYSTEM (71) Applicant: MASIMO CORPORATION, Irvine, CA (US)

(72) Inventors: Massi Joe E. Kiani, Laguna Niguel, CA (US); Michael O'Reilly, Cupertino, CA (US)

(73) Assignee: MASIMO CORPORATION, Irvine, CA (US)

( * ) Notice: Subject to any disclaimer, the term of this patent is extended or adjusted under 35 U.S.C. 154(b) by 78 days.

(21) Appl. No.: 14/479,083

(22) Filed: Sep. 5, 2014

(65) Prior Publication Data

US 2014/0378784 A1 Dec. 25, 2014

Related U.S. Application Data (63) Continuation of application No. 12/885,430, filed on Sep. 17, 2010, now abandoned.

(60) Provisional application No. 61/243,161, filed on Sep. 17, 2009.

(51) Int. Cl.
*A61B 5/1455* (2006.01)
*A61B 5/0402* (2006.01)
*A61B 5/0476* (2006.01)
*A61B 5/00* (2006.01)
*A61B 5/0205* (2006.01)

(52) U.S. Cl.
CPC .......... *A61B 5/1455* (2013.01); *A61B 5/0205* (2013.01); *A61B 5/0402* (2013.01); *A61B 5/0476* (2013.01); *A61B 5/4821* (2013.01)

(58) Field of Classification Search
CPC ... A61B 5/02055; A61B 5/024; A61B 5/1112; A61B 5/02125; A61B 5/0285
USPC .......... 604/65–67, 503, 890.1, 323
See application file for complete search history.

(56) References Cited

U.S. PATENT DOCUMENTS

| 4,421,122 | A | * | 12/1983 | Duffy ................ A61B 5/0484 600/544 |
| 4,960,128 | A | | 10/1990 | Gordon et al. |
| 4,964,408 | A | | 10/1990 | Hink et al. |
| 5,041,187 | A | | 8/1991 | Hink et al. |
| 5,069,213 | A | | 12/1991 | Polczynski |
| 5,163,438 | A | | 11/1992 | Gordon et al. |
| 5,286,252 | A | * | 2/1994 | Tuttle ................ A61K 31/135 604/20 |
| 5,319,355 | A | | 6/1994 | Russek |

(Continued)

OTHER PUBLICATIONS

Binnie, C. et al., Clinical Neurophysiology, vol. 2, 2003. Elvesier Science. p. 707-790.

(Continued)

*Primary Examiner* — Bhisma Mehta
*Assistant Examiner* — Matthew A Engel
(74) *Attorney, Agent, or Firm* — Knobbe, Martens, Olson & Bear LLP (57) ABSTRACT

A non-invasive, optical-based physiological monitoring system is disclosed. In an embodiment, the non-invasive, optical-based physiological monitoring system comprises an emitter configured to emit light into a tissue site of a living patient; a detector configured to detect the emitted light after attenuation by the tissue site and output a sensor signal responsive to the detected light; and a processor configured determine, based on the sensor signal, a first physiological parameter indicative of a level of pain of the patient.

8 Claims, 8 Drawing Sheets

(56) References Cited

U.S. PATENT DOCUMENTS

| | | | |
|---|---|---|---|
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| 5,441,528 A * | 8/1995 | Chang | A61N 1/40 600/26 |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A * | 2/1996 | Diab | A61B 5/14551 356/41 |
| 5,494,043 A | 2/1996 | O'Sullivan et al. | |
| 5,533,511 A | 7/1996 | Kaspari et al. | |
| 5,534,851 A | 7/1996 | Russek | |
| 5,544,661 A * | 8/1996 | Davis | A61B 5/0002 128/904 |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A * | 11/1999 | Kiani | A61B 5/14551 600/310 |
| 5,997,343 A | 12/1999 | Mills et al. | |
| 6,002,952 A | 12/1999 | Diab et al. | |
| 6,011,986 A | 1/2000 | Diab et al. | |
| 6,018,682 A * | 1/2000 | Rise | A61B 5/4094 607/45 |
| 6,027,452 A | 2/2000 | Flaherty et al. | |
| 6,036,642 A | 3/2000 | Diab et al. | |
| 6,045,509 A | 4/2000 | Caro et al. | |
| 6,047,203 A * | 4/2000 | Sackner | A41D 13/1281 600/301 |
| 6,067,462 A | 5/2000 | Diab et al. | |
| 6,081,735 A * | 6/2000 | Diab | G06K 9/0051 600/336 |
| 6,088,607 A | 7/2000 | Diab et al. | |
| 6,110,522 A | 8/2000 | Lepper, Jr. et al. | |
| 6,124,597 A | 9/2000 | Shehada | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A * | 12/2000 | Diab | G06K 9/0051 600/323 |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,301,493 B1 | 10/2001 | Marro et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 * | 2/2002 | Kiani | A61B 5/14551 439/909 |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 * | 6/2003 | Ali | A61B 5/14551 600/323 |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,631,291 B2 | 10/2003 | Viertio-Oja et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kianl et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,745,060 B2 | 6/2004 | Diab et al. | |
| 6,760,607 B2 | 7/2004 | Al-Ali | |
| 6,768,920 B2 * | 7/2004 | Lange | A61B 5/0478 600/300 |
| 6,770,028 B1 * | 8/2004 | Ali | A61B 5/0002 600/300 |

(56) References Cited

U.S. PATENT DOCUMENTS

| | | |
|---|---|---|
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 * | 8/2005 | Kiani ............... A61B 5/0478 600/324 |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,089,927 B2 * | 8/2006 | John ............... A61B 5/048 128/200.24 |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,146,211 B2 * | 12/2006 | Frei ............... A61B 5/04012 607/2 |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,277,758 B2 * | 10/2007 | DiLorenzo ......... A61N 1/36082 607/45 |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,299,088 B1 * | 11/2007 | Thakor ............... A61B 5/048 600/544 |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 * | 8/2008 | Al-Ali ............... A61B 5/14551 340/511 |
| 7,428,432 B2 * | 9/2008 | Ali ............... A61B 5/0002 600/323 |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 * | 5/2009 | Al Ali ............... A61B 5/0002 600/300 |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,715,919 B2 * | 5/2010 | Osorio ............... A61N 1/36014 607/45 |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,783,343 B2 * | 8/2010 | Sarkela ............... A61B 5/048 600/544 |
| 7,791,155 B2 | 9/2010 | Diab |
| 7,801,581 B2 | 9/2010 | Diab |
| 7,811,279 B2 * | 10/2010 | John ............... A61M 25/0026 604/890.1 |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |

(56) References Cited

U.S. PATENT DOCUMENTS

| | | | |
|---|---|---|---|
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 * | 8/2011 | Ali | A61B 5/0002 600/322 |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 * | 5/2012 | Kiani | A61M 16/12 604/131 |
| 8,185,180 B2 | 5/2012 | Diab et al. |
| 8,187,181 B2 * | 5/2012 | Osorio | A61B 5/048 128/920 |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 2002/0099409 A1 * | 7/2002 | Hui | A61G 7/05776 606/201 |

(56) References Cited

U.S. PATENT DOCUMENTS

| | | | |
|---|---|---|---|
| 2002/0173729 A1* | 11/2002 | Viertio-Oja | A61B 5/0476 600/544 |
| 2004/0015091 A1* | 1/2004 | Greenwald | A61B 5/02125 600/513 |
| 2004/0092809 A1* | 5/2004 | DeCharms | G01R 33/4806 600/410 |
| 2005/0113744 A1* | 5/2005 | Donoghue | A61F 2/72 604/66 |
| 2005/0277819 A1* | 12/2005 | Kiani | A61B 5/0478 600/324 |
| 2007/0010755 A1* | 1/2007 | Sarkela | A61B 5/048 600/544 |
| 2007/0021673 A1* | 1/2007 | Arbel | A61B 5/02 600/500 |
| 2007/0287931 A1* | 12/2007 | Dilorenzo | A61B 5/0476 600/545 |
| 2008/0033490 A1* | 2/2008 | Giftakis | A61B 5/0402 607/2 |
| 2008/0103375 A1* | 5/2008 | Kiani | A61B 5/0002 600/323 |
| 2008/0188760 A1* | 8/2008 | Al-Ali | A61B 5/14551 600/507 |
| 2008/0300471 A1* | 12/2008 | Al-Ali | A61B 5/14551 600/301 |
| 2008/0317672 A1* | 12/2008 | Viertio-Oja | A61B 5/0476 424/9.2 |
| 2009/0069642 A1* | 3/2009 | Gao | A61B 5/02055 600/300 |
| 2009/0099627 A1* | 4/2009 | Molnar | A61B 5/04014 607/62 |
| 2009/0264789 A1* | 10/2009 | Molnar | A61N 1/36135 600/544 |
| 2010/0030089 A1* | 2/2010 | Hyde | G06F 19/3481 600/508 |
| 2010/0100036 A1* | 4/2010 | Leuthardt | G06F 19/3481 604/65 |
| 2010/0261979 A1* | 10/2010 | Kiani | A61B 5/0002 600/301 |
| 2011/0087081 A1* | 4/2011 | Kiani | A61B 5/0002 600/301 |
| 2011/0172561 A1* | 7/2011 | Kiani | A61B 7/003 600/586 |
| 2011/0208018 A1* | 8/2011 | Kiani | A61B 5/0205 600/301 |
| 2011/0245633 A1* | 10/2011 | Goldberg | A61B 5/681 600/301 |
| 2015/0359489 A1* | 12/2015 | Baudenbacher | G06F 19/3418 600/300 |

OTHER PUBLICATIONS

Hager et al. The Perfusion Index Measured by a Pulse Oximeter Indicates Pain Stimuli in Anesthetized Volunteers, ASA Abstract 2003, Anesthesiology 2004; 101: A514.

Lopez-Silva et al. Transmittance Photoplethysmography and Pulse Oximetry with Near Infrared Laser Diodes, IMTC 2004—Instrumentation and Measurement, Technology Conference, May 2004.

Voss and Sleigh, Best Practice and Research Clinical Anaesthesiology, vol. 21, No. 3, pp. 313-325, 2007.

* cited by examiner

OPTICAL-BASED PHYSIOLOGICAL MONITORING SYSTEM

CROSS-REFERENCE TO RELATED APPLICATIONS

Any and all applications for which a foreign or domestic priority claim is identified in the Application Data Sheet as filed with the present application are hereby incorporated by reference under 37 CFR 1.57.

This application is a continuation of U.S. patent application Ser. No. 12/885,430, filed Sep. 17, 2010, and titled "Pharmacological Management System," which claims priority benefit under 35 U.S.C. §119(e) to U.S. Provisional Patent Application No. 61/243,161, filed Sep. 17, 2009, and titled "Pharmacological Management System." The entire disclosure of each of the above items is hereby made part of this specification as if set forth fully herein and incorporated by reference for all purposes, for all that it contains.

BACKGROUND

Generation and analysis of an electroencephalogram (EEG) is a widely accepted noninvasive procedure for diagnosing a person's neurological system. For example, an EEG can reflect changes in a brain's cellular function due to insufficient oxygen or drugs, to name a few. An EEG system consists of a bio-potential sensor and corresponding monitor to process, analyze and display an EEG signal and corresponding neurological parameters. A bio-potential sensor responds to the electrical potential difference between at least two well-spaced electrodes, using a separate ground electrode. The biopotential monitor typically displays the EEG waveform and a numerical index that reflects changes in the EEG bandwidth and power.

Generation and analysis of a photoplethysmograph is a widely accepted noninvasive procedure for diagnosing a person's cardiovascular system. For example, a photoplethysmograph can yield the oxygen saturation level of arterial blood, an indicator of a person's oxygen supply. A pulse oximetry system consists of an optical sensor applied to a fleshy tissue site, such as a fingertip, and a corresponding pulse oximetry monitor (pulse oximeter). Using multiple wavelength light emitting diodes and a corresponding detector, the optical sensor measures the light absorption of the pulsatile blood at the tissue site. In particular, the optical sensor is responsive to the instantaneous blood volume as well as the blood constituency. Accordingly, the pulse oximeter typically displays a numerical readout of a person's oxygen saturation and pulse rate along with an audible indication of the person's pulse. The photoplethysmograph waveform may also be displayed.

Conventional pulse oximetry assumes that arterial blood is the only pulsatile blood flow in the measurement site. During patient motion, venous blood also moves, which causes errors in conventional pulse oximetry. Advanced pulse oximetry processes the venous blood signal so as to report true arterial oxygen saturation and pulse rate under conditions of patient movement. Advanced pulse oximetry also functions under conditions of low perfusion (small signal amplitude), intense ambient light (artificial or sunlight) and electrosurgical instrument interference, which are scenarios where conventional pulse oximetry tends to fail.

Advanced pulse oximetry is described in at least U.S. Pat. Nos. 6,770,028; 6,658,276; 6,157,850; 6,002,952; 5,769,785 and 5,758,644, which are assigned to Masimo Corporation ("Masimo") of Irvine, Calif. and are incorporated by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are also assigned to Masimo and are also incorporated by reference herein. Advanced pulse oximetry systems including Masimo SET® low noise optical sensors and read through motion pulse oximetry monitors for measuring $SpO_2$, pulse rate (PR) and perfusion index (PI) are available from Masimo. Optical sensors include any of Masimo LNOP®, LNCS®, SofTouch™ and Blue™ adhesive or reusable sensors. Pulse oximetry monitors include any of Masimo Rad-8®, Rad-5®, Rad®-5v or SatShare® monitors.

Advanced blood parameter measurement systems are described in at least U.S. Pat. No. 7,647,083, filed Mar. 1, 2006, titled *Multiple Wavelength Sensor Equalization*; U.S. Pat. No. 7,729,733, filed Mar. 1, 2006, titled *Configurable Physiological Measurement System*; U.S. Pat. Pub. No. 2006/0211925, filed Mar. 1, 2006, titled *Physiological Parameter Confidence Measure* and U.S. Pat. Pub. No. 2006/0238358, filed Mar. 1, 2006, titled *Noninvasive Multi-Parameter Patient Monitor*, all assigned to Masimo Laboratories, Irvine, Calif. (Masimo Labs) and all incorporated by reference herein. Advanced blood parameter measurement systems include Masimo Rainbow® SET, which provides measurements in addition to $SpO_2$, such as total hemoglobin (SpHb™), oxygen content (SpOC™) methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad-87™ and Rad-57™ monitors, all available from Masimo. Such advanced pulse oximeters, low noise sensors and advanced blood parameter systems have gained rapid acceptance in a wide variety of medical applications, including surgical wards, intensive care and neonatal units, general wards, home care, physical training, and virtually all types of monitoring scenarios.

SUMMARY

Depth of consciousness (DOC) is an important physiological assessment during the administration of anesthesia and analgesia drugs. For example, an overdose of anesthesia risks physical impairment or death. An underdose of anesthesia risks "surgical awareness." A DOC index is typically derived by an EEG sensor measurement of electrical activity in the cerebral cortex. Advantageously, the measurement of various cardio-vascular system and respiratory system responses can substitute for or supplement typical central nervous system measures of consciousness, providing improved resolution and accuracy. For example, cardiovascular system and respiratory system parameters responsive to consciousness may include perfusion index (PI), plethysmograph variability index (PVI), heart rate (HR), blood pressure (BP) and respiration rate (RR), to name a few.

Level of pain (LOP) is also an important physiological assessment during anesthesia and analgesia. A LOP index is an advantageous quantization of pain that allows proper dosing of administered drugs. Advantageously, a LOP index may also be derived from various cardiovascular system and respiratory system parameters, such as those cited above.

Although dissimilar physiological phenomena, there is an important relationship between consciousness and pain for anesthesia and analgesia applications. During anesthesia, it is desirable to ensure that pain is eliminated during apparent unconsciousness. During analgesia, it is desirable for pain to be diminished or eliminated without impinging on consciousness. Accordingly, parameters useful in conjunction with consciousness assessment may be useful in conjunction with pain assessment and vice-a-versa.

A pharmacological management system advantageously provides sensors and processors to measure and analyze both DOC and LOP. Accordingly, a pharmacological management system advantageously senses and analyzes both consciousness and pain related physiological signals so as to generate multidimensional parameters or indexes indicative of both physiological processes.

One aspect of a pharmacological management system comprises sensors, a pharmacological status monitor and a drug administrator. The sensors attach to the patient so as to generate corresponding sensor signals. The pharmacological status monitor is responsive to the sensor signals so as to generate an output indicative of the drug-induced effects of the pharmacological agent on the patient. Further, the monitor output is fed-back to the drug administrator so as to regulate administration of the agent for a desired effect.

In various embodiments, the monitor comprises a hematological processor responsive to an optical sensor signal and a neurological processor responsive to a bio-potential sensor. The hematological processor has a photoplethysmograph input and provides a level of pain output to the pharmacological status monitor. The neurological processor has an EEG input and provides a depth of consciousness output to the pharmacological status monitor. The pharmacological status monitor generates a control output to a drug-infusion pump. The level of pain output is a perfusion index. The pharmacological status monitor generates a combined index related to both depth of consciousness and level of pain.

Another aspect of a pharmacological management system is inputting sensor signals derived from a patient and calculating physiological parameters accordingly. The sensor signals provide measurements of physiological systems. Physiological parameters are calculated from the sensor signals. The parameters are operated on to generate monitor outputs, which are indicative of levels of both consciousness and pain.

In various embodiments, a first sensor signal is utilized to generate a consciousness index and a second sensor signal is utilized to generate a perfusion index. Cues are displayed to indicate a patient with a stable or unstable physiological condition. Outputs control drug-infusion equipment or medical gas ventilation equipment. Patient wellness is diagnosed.

A further aspect of a pharmacological management system measures physiological parameters derived from at least some of a patient's central nervous system, respiratory system and cardio-vascular system so as to assess level of pain and depth of consciousness during the administration of anesthetic and analgesic agents. The pharmacological management system comprises sensors in communications with a patient so as to generate sensor signals and a monitor front-end in communications with the sensor signals so as to generate digitized sensor signals. A signal processor is in communications with the front-end so as to generate physiological parameters. The signal processor derives an electrical-based depth of consciousness (DOC) indicator from an electrical one of the sensors in communications with the patient's central nervous system and a pleth-based level of pain (LOP) indicator from an optical one of the sensors in communications with the patient's cardio-vascular system. An instrument manager generates a monitor output in response to a combination of the DOC indicator and the LOP indicator.

In various embodiments, a drug administrator administers a pharmacological agent to the patient and is responsive to the monitor output. The LOP indicator is responsive to a perfusion index (PI) parameter or a plethysmograph variability index (PVI) parameter. The monitor output comprises an electronic signal to the drug administrator that affects the dose of pharmacological agent. The monitor output also comprises a combined display of LOP and DOC.

DETAILED DESCRIPTION

Figure 1:
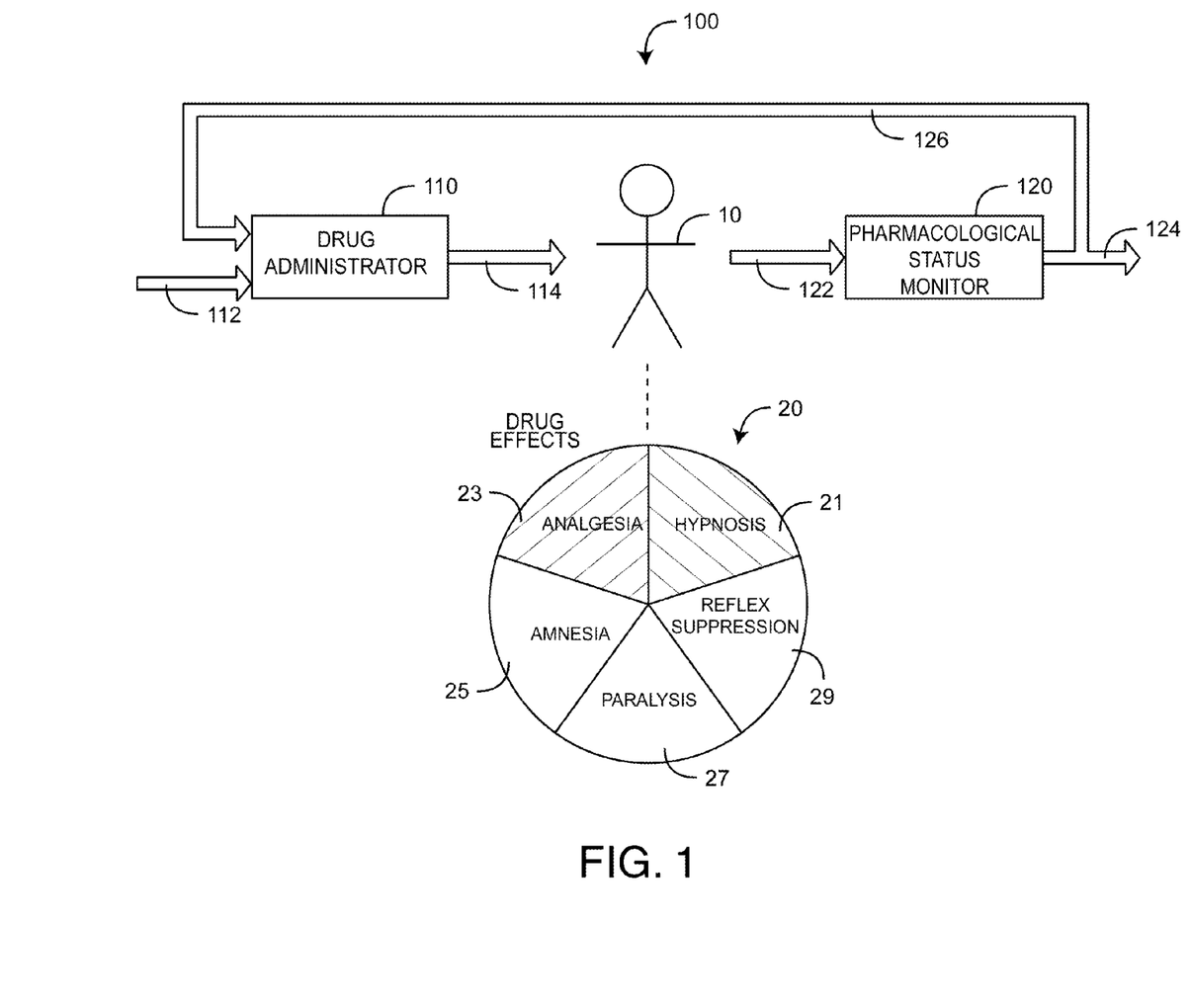
FIG. 1 is a general block diagram of pharmacological management system.

FIG. 1 generally illustrates a pharmacological management system 100 having a drug administrator 110 that provides a pharmacological agent 114 to a patient 10 and a pharmacological status monitor 120 responsive to corresponding drug-induced effects 20. Pharmacological agents 114 may be, as examples, anesthesia or analgesia drugs. For anesthesia applications, the desired effect 20 may be general anesthesia or various levels of sedation. The drug administrator 110 may vary from a healthcare provider manually administering drugs to an automatic or semi-automatic machine such as a drug infusion device or medical gas inhalation device. The drug administrator may be responsive to external controls 112, such as manual inputs or electronic signals.

As shown in FIG. 1, drug-induced effects 20 in the patient 10 may include hypnosis 21, analgesia 23, amnesia 25, paralysis 27 and reflex suppression 29. Hypnosis 21 produces unconsciousness; analgesia 23 blocks the conscious sensation of pain; amnesia 25 prevents memory formation; paralysis 27 prevents unwanted movement or muscle tone; and reflex suppression 29 prevents exaggerated autonomic reflexes. For general anesthesia, some or all of these drug-induced effects 20 may be the goal. For low-level sedation, the goal may be to achieve some effects 20 while suppressing others. For pain reduction, analgesia 23 is the goal along with minimization of other drug-induced effects 20.

Also shown in FIG. 1, the pharmacological management system 100 advantageously assists healthcare providers to achieve the above-stated goals, among others. Sensors (not shown) attached to the patient 10 provide biological signals 122 to the pharmacological status monitor 120. The monitor 120 processes these signals 122 and generates outputs 124 indicative of the effects 20 of administered pharmacological agents 114. The outputs 124 may be displays, alarms, controls or indicators, for example. The outputs 124 may also provide manual or automatic feedback 126 to the drug administrator 110 so as to regulate administration of the agent 114 for the desired effects 20.

Figure 2:
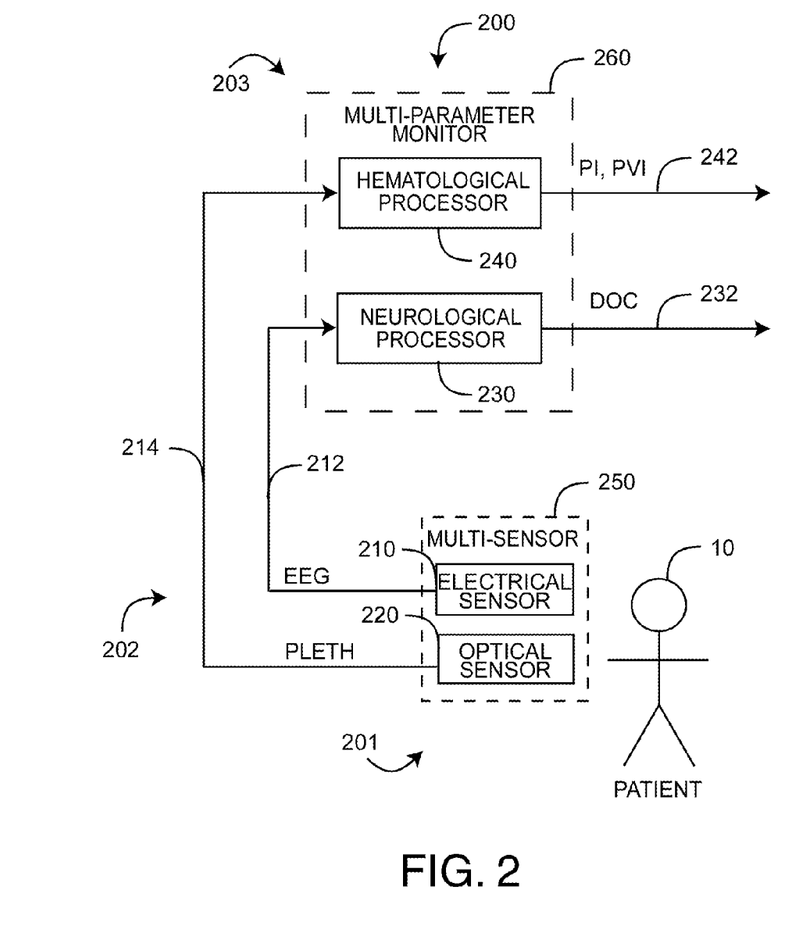
FIG. 2 is a block diagram of a pharmacological management system embodiment responsive to electrical and optical sensors so as to measure consciousness and pain.

FIG. 2 illustrates a pharmacological management system 200 having sensors 201 in communications with a patient 10. The sensors 201 generate sensor waveforms 202 to corresponding monitors 203. The monitors 203 process the waveforms 202 so as to calculate parameters that alone or in combination are indicative of the pharmacological status of the patient 10. In one embodiment, sensors 201 include an electrical (biopotential) sensor 210 placed proximate the head so as to generate an EEG waveform 212 and an optical sensor 220 placed on a fleshy tissue site so as to generate a photoplethysmograph 214.

A neurological monitor 230 processes the EEG waveform 212 to generate a first parameter 232 related to depth of consciousness (DOC). In an embodiment, the first parameter 232 is a dimensionless index that reflects the level of activity of the cerebral cortex. In a particular embodiment, the first parameter 232 is a Bispectral Index™ (BIS) proprietary to Aspect Medical Systems, Inc., Norwood, Mass. ("Aspect"), and the neurological processor 230 is a BIS module also proprietary to Aspect. In another particular embodiment, the first parameter 232 is a Patient State Index™ (PSI) proprietary to Hospira, Inc., Lake Forest, Ill. ("Hospira"), and the neurological processor 230 is a SEDLine monitor or module, also proprietary to Hospira.

A hematological monitor 240 processes the photoplethysmograph (pleth) waveform 214 to generate at least one second parameter 242. In an embodiment, the second parameter is a level of pain (LOP) index. In an embodiment, the second parameter is a pleth-based DOC index providing improved resolution and accuracy in determining DOC compared to only an EEG-based DOC index. In an embodiment, the second parameter 242 is a Perfusion Index (PI) or a Plethysmograph Variability Index (PVI) proprietary to Masimo Corporation, Irvine, Calif. ("Masimo") or both, and the hematological processor 240 is any of various monitors or modules available from Masimo, such as described above. PI may change dramatically in response to sympathetic changes in vasoconstriction or vasodilation of peripheral vessels reflective of consciousness or pain. PI comprises a relative indication of pulse strength at a monitoring site. For example, PI may be defined as the ratio of a pleth AC value to its DC value, or the percentage of pulsatile signal to non-pulsatile signal. PVI is described in U.S. patent application Ser. No. 11/952,940 filed Dec. 7, 2007 titled *Plethysmograph Variability Index*, assigned to Masimo and incorporated by reference herein.

As shown in FIG. 2, in an embodiment the electrical sensor 210 is any of various EEG sensors having multiple biopotential electrodes for placement across various head sites for detection of electrical signals originating in the brain. In an embodiment, the optical sensor 220 is any of various blood parameter sensors having LED emitters and at least one photodiode detector for placement at various fleshy tissue sites for detection of pulsatile blood flow and in particular the measurement of optical properties thereof, such as absorption, reflection, transmission and transflectance to name a few. In an embodiment, the optical sensor 220 is any of various optical sensors available from Masimo, such as described above.

Further shown in FIG. 2, in an embodiment, and optical sensor may comprise a combination or multi-sensor 250 that provides both EEG and photoplethysmograph waveforms, such as described with respect to FIGS. 5 and 8, below. In an embodiment, the hematological and neurological monitors may comprise a combination or multi-parameter monitor 260 having hematological and neurological processing plug-ins, modules or similar technology, such as described with respect to FIGS. 6 and 7, below.

Figure 3:
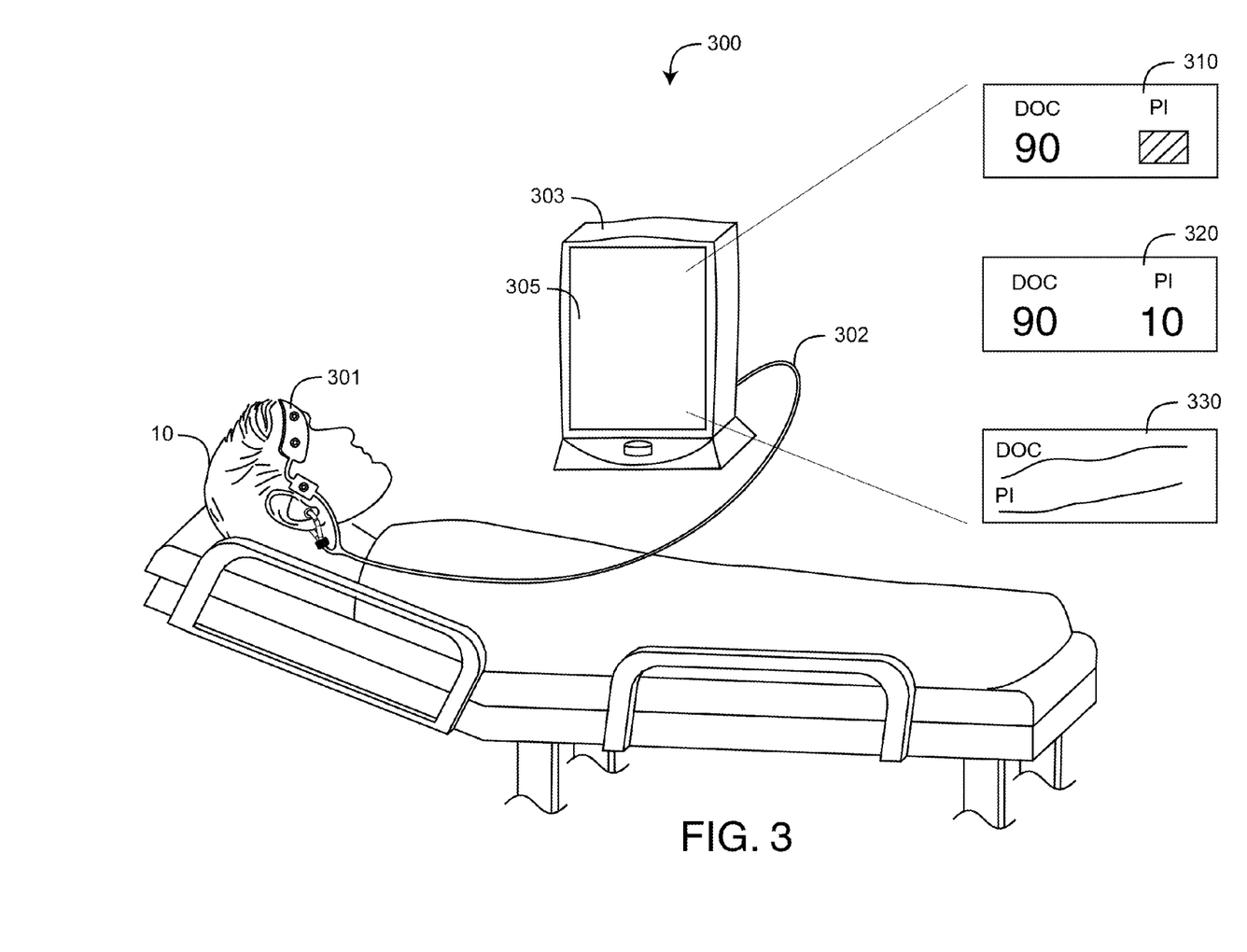
FIG. 3 illustrates a pharmacological management system configured for anesthesia applications.

FIG. 3 illustrates a pharmacological management system 300 configured for anesthesia applications having a sensor 301 attached to a patient 10, a pharmacological status monitor 303 and a sensor cable 302 providing sensor signal communications between the sensor 301 and the monitor 303. In an embodiment, the sensor 301 provides multiple physiological signals to the monitor 303, which derives at least two different measures of consciousness or at least a measurement of consciousness and a measurement of pain. In an embodiment, these physiological signals are EEG and photoplethysmograph signals. In an embodiment, the monitor 303 calculates both a DOC index and PI from the EEG and plethysmograph signals and displays these parameters on the monitor display 305 accordingly.

As shown in FIG. 3, in a mixed display embodiment 310 a DOC parameter is displayed numerically adjacent a LOP parameter displayed as a color. For example, the DOC parameter may be an index, such as BIS, displayed as a dimensionless number. The LOP parameter may be, for example, PI, displayed as a green, yellow or red indicator depending on a preset range of high, medium and low PI values. The low PI value range being set so as to indicate the occurrence of significant vasoconstriction in response to pain or measurable vasodilation in response to increasing depth of consciousness. In a numerical display embodiment 320, DOC and LOP are displayed as proximately located numerical readouts, such as a DOC index and a perfusion index (PI). In a graphical display embodiment 330, DOC and LOP are separately indicated as trends, such as a DOC index trend and a PI trend. The monitor may also calculate a combined index related to consciousness or pain or both. Other individual or combined parameter displays include any of various readouts, graphs, charts or indicators in any of various single or multiple colors. The above monitoring and display embodiments advantageously assist an anesthesiologist or other administrator of drugs to titrate anesthesia based upon either multiple indicators of DOC or on indicators of DOC and LOP. This dual monitoring of pain and consciousness during administration of anesthesia drugs advantageously increases monitor responsivity to under or over dosing of anesthesia.

Figure 4:
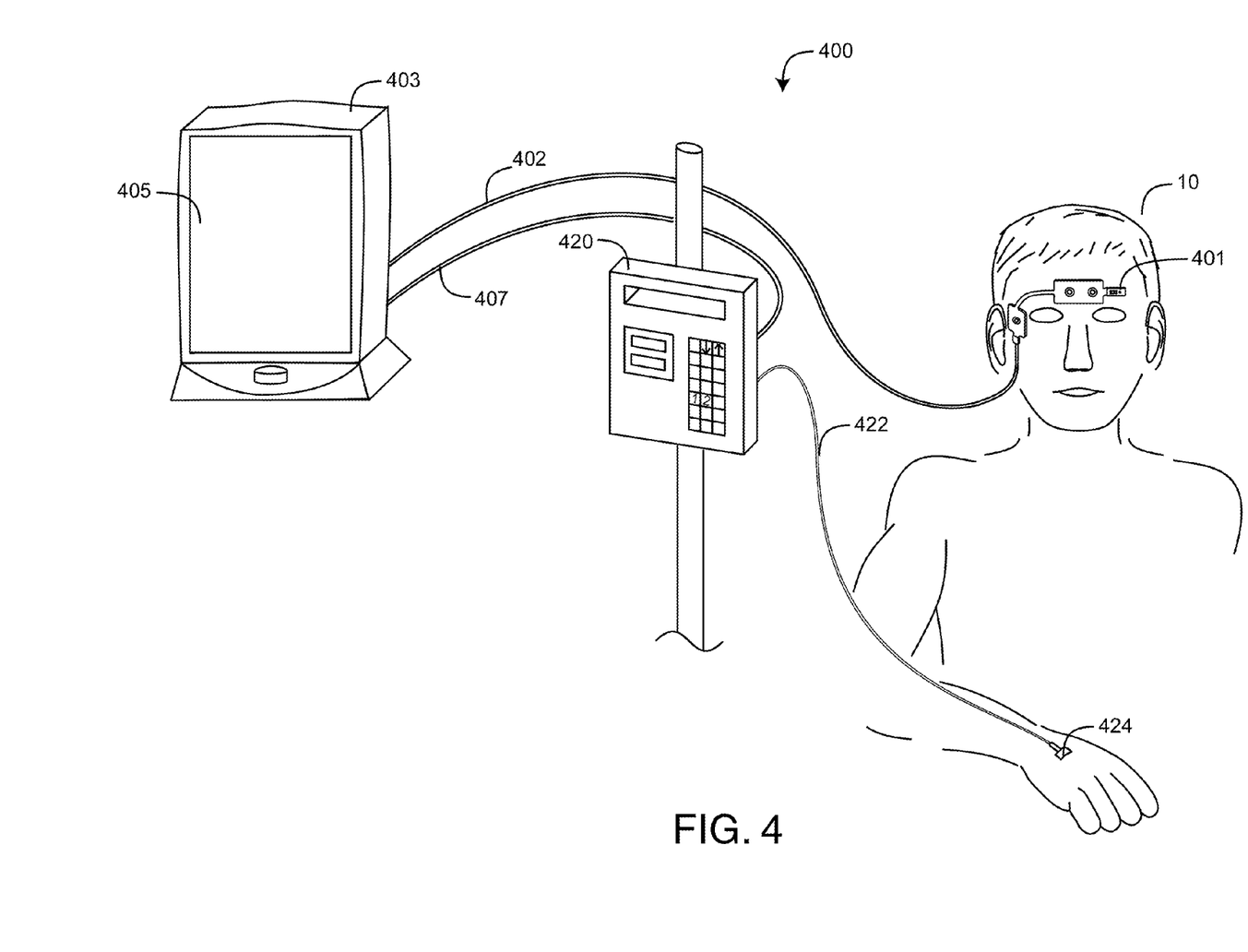
FIG. 4 illustrates a pharmacological management system configured for analgesia applications.

FIG. 4 illustrates a pharmacological management system 400 configured for analgesia applications, such as patient controlled analgesia (PCA). In particular, the pharmacological management system 400 has a sensor 401 attached to a patient 10, a pharmacological status monitor 403 and a sensor cable 402 providing sensor signal communications between the sensor 401 and the monitor 403. Further, the monitor 403 generates control signals via a control cable 407 to the drug-infusion pump 420. The drug-infusion pump 420 administers drugs to the patient 10 via a tube 422 and an IV 424. A patient-actuated controller (not shown) generates drug administration requests to the drug-infusion pump 420 via cable or wireless communications. In this manner, the pump 420 responds to patient perceived pain levels. In particular, the patient 10 actuates the controller, such as via a button press, so as to signal the drug-infusion pump 420 to administer a measured analgesia dose. The pump 420 enables or pauses patient-controlled dosing according to monitor 403 signals transmitted via the control cable 407. These control signals are responsive to monitor calculated DOC and LOP related parameters. Further, these parameters are displayed on a monitor screen 405, such as described with respect to FIG. 3, above.

The sensor 401 provides physiological signals to the monitor 403 related to depth of consciousness (DOC) or level of pain (LOP). In an embodiment, these physiological signals are EEG and photoplethysmograph signals. The monitor 403 calculates DOC, LOP or a combination consciousness and pain parameters from the EEG and plethysmograph signals and processes those parameters to generate control outputs 407 to the drug-infusion pump 420. In this manner, the administration of analgesia is controlled not only according to the patient's perceived pain level, but also according to a physiologically indicated pain level and to avoid consciousness impairment. In a particular embodiment, LOP is indicated by a perfusion index (PI), as described above, and PCA is paused or enabled according to a rising or falling PI, respectively, or according to a DOC index, or both.

Figure 5A:
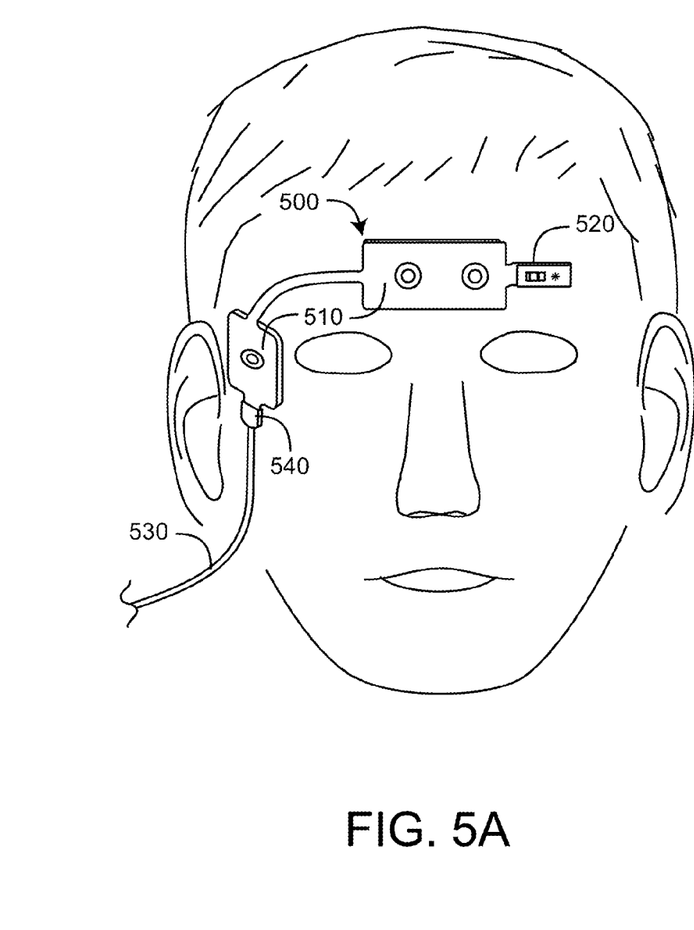
FIGS. 5A-B are illustrations of combination sensor embodiments for measuring both consciousness and pain.
Figure 5B:
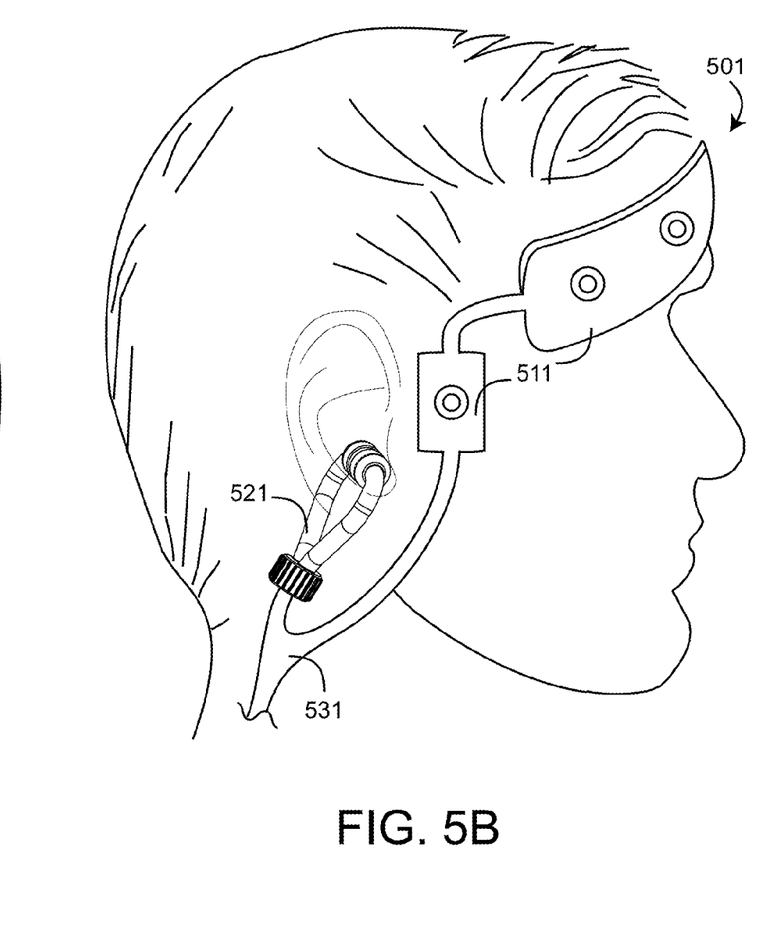

FIGS. 5A-B illustrate combination sensors, which provide inputs to a pharmacological status monitor having both hematological and neurological signal processors, such as described with respect to FIG. 2, above. FIG. 5A illustrates a combination sensor 500 applied to the forehead and temple areas of a person. The sensor 500 includes an electrical or more specifically a biopotential sensor 510 and an optical sensor 520. A patient cable 530 connects the sensor to one or more monitoring devices (not shown), such as described with respect to FIGS. 7A-E, below. The biopotential sensor 510 may be an EEG sensor for depth of consciousness monitoring, as described above. The optical sensor 520 may be a pulse oximetry reflectance sensor for consciousness or pain monitoring via perfusion index (PI) or other blood parameter, also as described above. The patient cable 530 may connect near the person's temple, as shown, or as an alternative near the person's forehead. The biopotential sensor 510 and optical sensor 520 may share a common connector 540 or each sensor may have a dedicated patient cable connector. Combination EEG and pulse oximetry sensors are described in U.S. Pat. No. 6,934,570, issued Aug. 23, 2005, titled *Physiological Sensor Combination* and incorporated by reference herein.

FIG. 5B illustrates a combination sensor 501 applied to the forehead, temple and ear concha areas of a person. In one embodiment, the sensor 501 includes a biopotential sensor 511, an optical sensor 521 and a cable 531 that connects the sensor 501 to one or more monitoring devices (not shown). The biopotential sensor 511 may be an EEG sensor for depth of consciousness monitoring, as described above. The optical sensor 521 may be a pulse oximetry transmissive sensor for level of pain monitoring via perfusion index (PI) or other blood parameter, also as described above. In a particular embodiment, the optical sensor 521 is a "Y"-clip ear sensor that flexes so as to slide over the ear periphery and onto either side of the concha. An emitter and detector located at opposite clip ends can then transmit multiple wavelength light into the concha tissue and detect that light after attenuation by pulsatile blood flow within the concha tissue. Optical ear sensors are described in U.S. Provisional Patent App. No. 61/152,964, filed Feb. 16, 2009, titled *Ear Sensor* and incorporated by reference herein.

Figure 6:
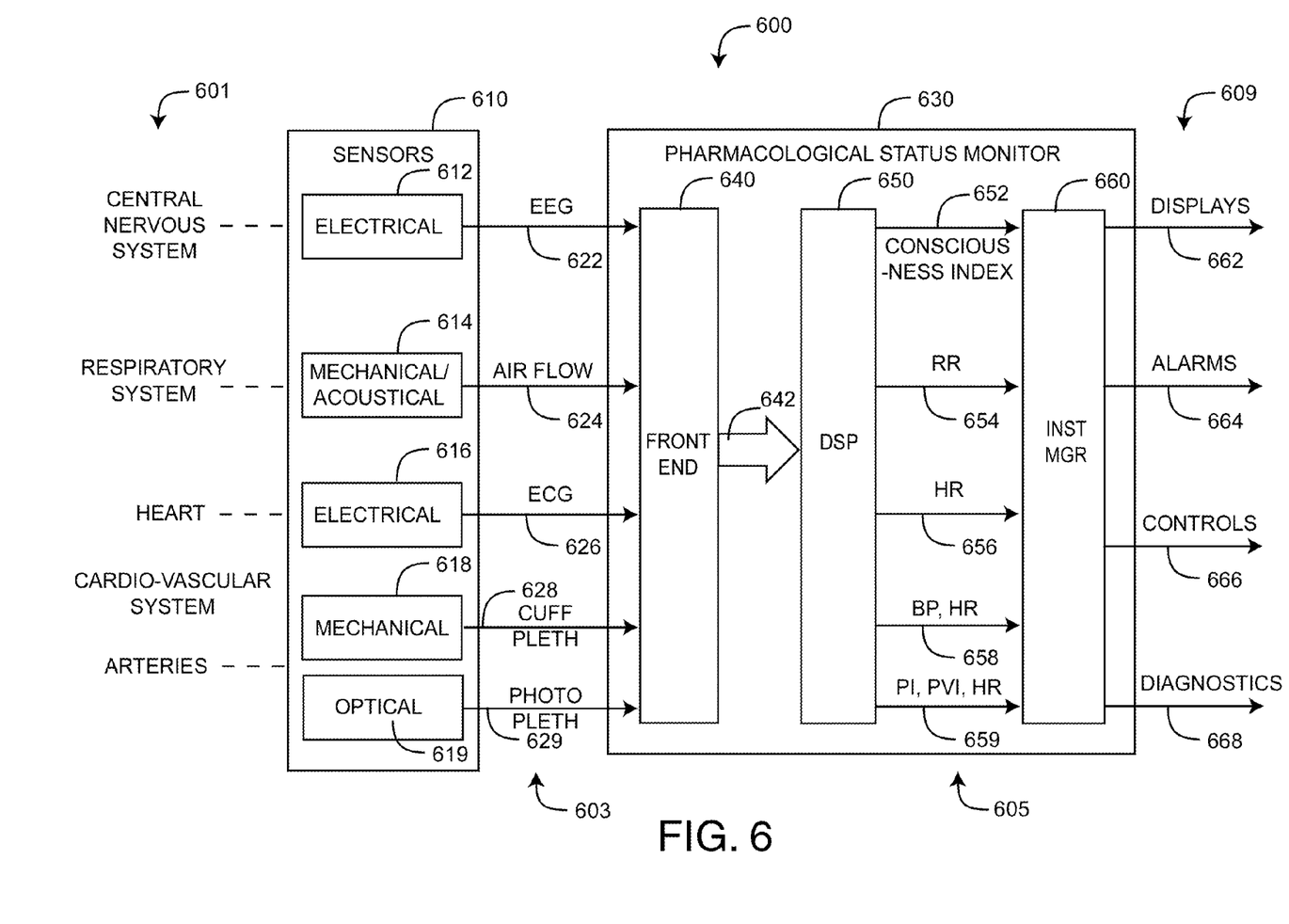
FIG. 6 is a detailed block diagram of a pharmacological management system embodiment.
Figure 7A:
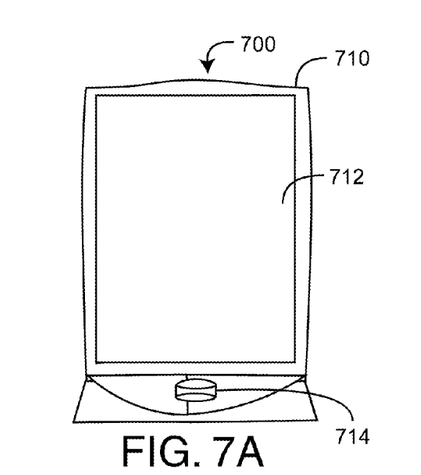
FIGS. 7A-E are illustrations of a pharmacological status monitor embodiment responsive to various sensors.
Figure 7B:
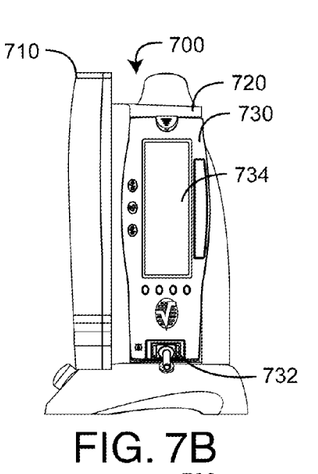
Figure 7C:
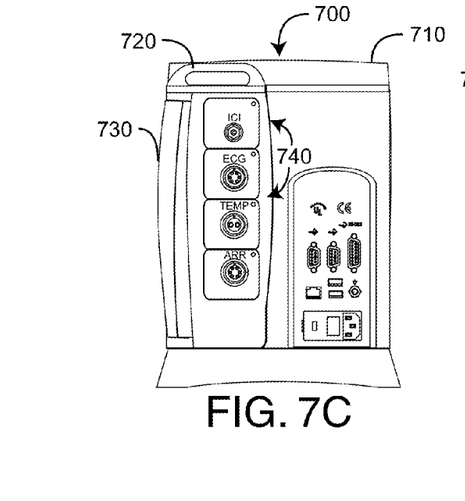
Figure 7D:
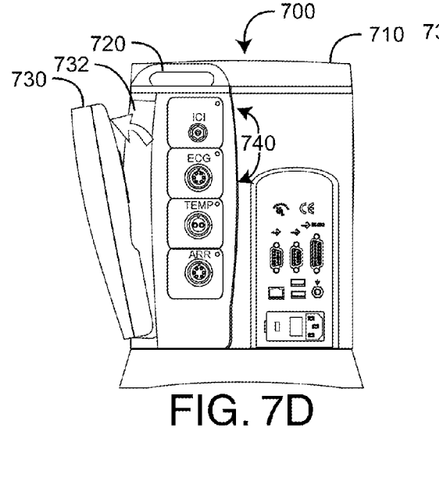
Figure 7E:
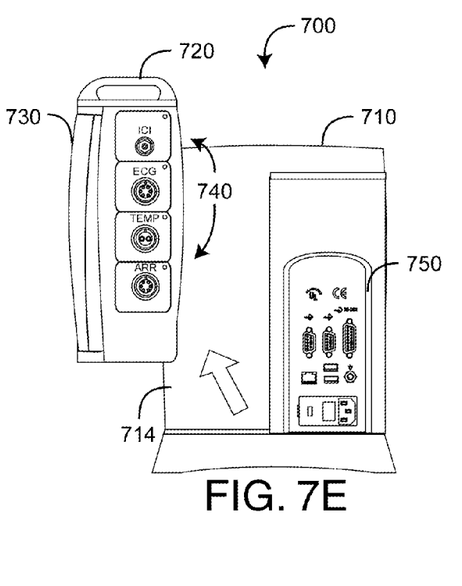

FIG. 6 illustrates a pharmacological management system 600 embodiment having multiple sensors 610 in communication with a pharmacological status monitor 630. The sensors 610 are responsive to various physiological systems 601 so as to generate various sensor signals 603. A pharmacological status monitor 630 derives physiological parameters 605 from the sensor signals 603 and operates on the parameters 605 to generate monitor outputs 609. The measured physiological systems 601 include one or more of the central nervous system, including the brain; the respiratory system, including the lungs; and the cardio-vascular system, including the heart and arteries. The sensors 610 may include electrical sensors 612, 616, such as bio-potential sensors that generate EEG 622 and ECG 626 signals in response to brain or heart activity, respectively. The sensors 610 may also include mechanical, acoustical, temperature or humidity sensors 614, to name a few, that directly or indirectly measure the inspired or expired air flow 624 from the lungs. Sensors 610 include mechanical sensors 618 that measure arterial blood pressure 628. Sensors 610 further include optical sensors 619 that measure arterial blood flow or volume 629, according to instantaneous light absorption.

Also shown in FIG. 6, parameters 605 are any derived measurements indicative of consciousness or pain or both. Parameters 605 may include a consciousness index 652 derived from an EEG signal 622, such as described with respect to FIG. 2, above. Parameters 605 may also include a perfusion index (PI) 659 indicative of pain and derived from a photoplethysmograph signal 629, also described with respect to FIG. 2, above. Other pain indicative parameters may include respiration rate (RR) 654 derived from a respiratory air flow signal 624; heart rate (HR) 656, 658, 659 derived from an ECG 626, cuff plethysmograph 628 or photoplethysmograph 629; and blood pressure (BP) 658 derived from a pressure plethysmograph 628.

In addition, FIG. 6 shows outputs 609 including displays 662, alarms 664, controls 666 and diagnostics 668. Alarms 664 may be, for example, audible or visual alerts warning of critical conditions that need immediate attention. Controls 666 may be any of various electrical or electronic, wired or wireless or mechanical outputs, to name a few, capable of interfacing with and affecting another device. As examples, controls 666 may interface with drug-infusion equipment or medical gas ventilation equipment, as described above. Diagnostics, including wellness indices, may be audible or visual cues indicating a patient with a stable or unstable physiological condition. Visual cues may be any of various digital readouts, bar graphs, trend graphs, color indicators and the like. Audible cues may be any of various sounds or tones, whether intermittent or continuous or constant or varying in volume.

As shown in FIG. 6, the monitor 630 has a sensor front end 640, one or more digital signal processors (DSP) 650 and one or more instrument managers 660. In an embodiment, the sensor front end 640 may have one or more of various preamps, signal conditioning and analog-to-digital conversion (ADC) that amplify, filter and digitize the sensor signals 603 so as to output digital data channels 642 to a DSP 650. In an embodiment, the DSP 650 comprises a processing device, such as one based on the Super Harvard ARChitecture ("SHARC") commercially available from Analog Devices or any other of a wide variety of data and/or signal processors capable of executing programs for determining physiological parameters from input data. In particular, the DSP 650 includes program instructions capable of receiving multiple channels of data 642 from the sensor front end 640, each channel of which relates to one or more sensor signals 603.

Also shown in FIG. 6, the instrument manager 660 may comprise one or more microcontrollers controlling system management, including, for example, translation and communications of calculated parameter data 605 to various outputs 609. The instrument manager 660 may also act as a watchdog circuit by, for example, monitoring and controlling the activity of the DSP 650.

FIG. 7A-E illustrate a pharmacological status monitor 700 embodiment capable of inputting signals from a wide range of sensors and of deriving a wide range of physiological parameters therefrom including DOC and LOP parameters, such as BIS and PI described with respect to FIG. 2, above, and others described with respect to FIG. 6, above. The pharmacological status monitor 700 has a docking station 710 including a display 712, a removable shuttle 720, a removable handheld 730 and a combination of plug-in modules 740. The docking station 710 has a shuttle port 714 that allows the shuttle station 720 to dock. The shuttle station 720 has a handheld port 732 that allows the handheld monitor 730 to dock. Accordingly, the modular patient monitor 700 has three-in-one functionality including a handheld 730, a handheld 730 docked into a shuttle station 720 as a handheld/shuttle combination and a handheld/shuttle docked into a docking station 710. When docked, the three modules of handheld 730, shuttle 720 and docking station 710 function as one unit. The handheld 730 docked into the shuttle module 720 functions independently of the docking station 710 and expands the handheld parameter capability to the ability to measure all parameters available to the shuttle 720. The docking station 710, in turn, provides the shuttle 720 or handheld/shuttle combination with a large color display 712 and trim knob control 714 in addition to a power supply/communications module 750 having ports for wireless and hardwired communications, Internet access and printers. In an embodiment, the handheld monitor 730 incorporates blood parameter measurement technologies including $SpO_2$, PI, HbCO, HbMet, and Hbt, and the shuttle station 720 incorporates non-blood parameters, such as intelligent cuff inflation (101) for blood pressure measurements, acoustic respiration rate (ARR), ECG and EEG to name a few. A multi-parameter monitor is described in U.S. patent Ser. No. 11/903,746, filed Sep. 24, 2007, titled *Modular Patient Monitor* and incorporated by reference herein.

Figure 8:
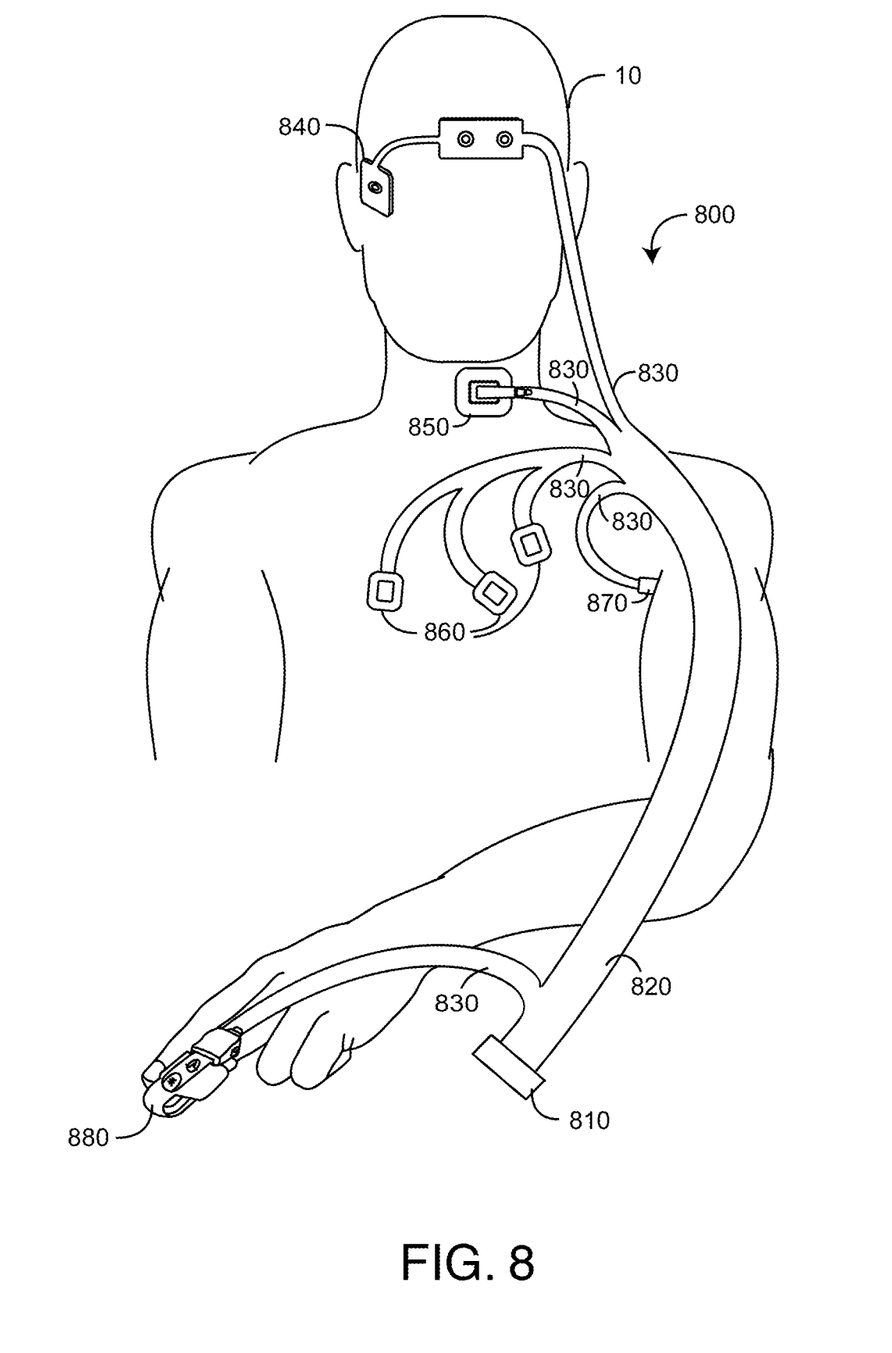
FIG. 8 is an illustration of a multi-sensor embodiment for measuring level of pain and depth of consciousness.

FIG. 8 illustrates an integrated multi-sensor 800 advantageously configured to provide multiple physiological parameter measurements to a pharmacological status monitor 700 (FIGS. 7A-E) via a single connector and interconnected patient cable (not shown). This eliminates the difficulties of a large number of cables and cumbersome connectors when multiple sensors are placed on various areas of a person. In particular, the multi-sensor 800 has a connector 810 in communications with a trunk 820, which fans out to multiple branches 830, each of which terminates in a sensor 840, 850, 860, 870, 880. In an embodiment, the multi-sensor allows measurement of perfusion index (PI) via a pulse oximetry sensor 880 placed on a finger; skin temperature via a thermistor 870 located under an arm; heart rate (HR) via an ECG sensor 860 placed on the chest area; respiration rate (RR) via an acoustic sensor 850 located on the neck to detect airway sounds; and a consciousness index via an EEG sensor 840 placed on the head area.

In other embodiments, other multiple parameter sensors provide sensor inputs to a pharmacological status monitor. A sensor providing both optical and acoustic inputs for blood parameters and acoustic parameters, such as discussed above, in addition to cerebral oximetry, oxygen supply and metabolism among other parameters is described in U.S. Provisional Patent App. No. 61/350,673 titled Opticoustic Sensor filed Jun. 2, 2010, assigned to Masimo and incorporated by reference herein. In particular, the cerebral parameters measured by the opticoustic sensor disclosed therein may provide further indications of LOP and DOC.

A pharmacological management system has been disclosed in detail in connection with various embodiments. These embodiments are disclosed by way of examples only and are not to limit the scope of the claims that follow. One of ordinary skill in the art will appreciate many variations and modifications.

What is claimed is:

1. A physiological monitoring system comprising:
   a non-invasive optical sensor comprising:
      an emitter configured to emit light into a tissue site of a living patient; and
      a detector configured to detect the emitted light after attenuation by the tissue site and output a first sensor signal responsive to the detected light;
   one or more bio-potential sensors configured to be attached to the patient and configured to output at least a second sensor signal and a third sensor signal;
   an additional sensor configured to be attached to the patient and configured to output at least a fourth sensor signal; and
   a processor configured to:
      determine, based on the first sensor signal, a first physiological parameter indicative of a level of pain of the patient, wherein the first physiological parameter comprises a perfusion index;
      determine, based on the second sensor signal, a second physiological parameter indicative of the level of pain of the patient, wherein the second physiological parameter comprises an ECG;
      determine, based on the third sensor signal, a third physiological parameter indicative of a depth of consciousness of the patient, wherein the third physiological parameter comprises an EEG;
      determine, based on at least one of the first sensor signal, the second sensor signal, the third sensor signal, or the fourth sensor signal, a plurality of additional physiological parameters indicative of at least one of the level of pain of the patient or the depth of consciousness of the patient, wherein the plurality of additional physiological parameters include at least one of a respiration rate, a respiratory air flow, a heart rate, or a blood pressure; and
      determine, based on the first physiological parameter, the second physiological parameter, the third physiological parameter, and the plurality of additional physiological parameters, a combined index indicative of both the level of pain and the depth of consciousness of the patient.

2. The physiological monitoring system of claim 1, wherein the processor is further configured to determine, based on the first physiological parameter and the second physiological parameter, a combined indication of the level of pain of the patient.

3. The physiological monitoring system of claim 1, wherein the processor is further configured to determine, based on the first physiological parameter, the second physiological parameter, and the third physiological parameter, a combined indication of both the level of pain and the depth of consciousness of the patient.

4. The physiological monitoring system of claim 1 further comprising:
   a monitor comprising the processor,
   wherein the non-invasive optical sensor, the one or more bio-potential sensors, and the additional sensor are in communication with the monitor via a single cable.

5. The physiological monitoring system of claim 1 further comprising:
a drug administration device configured to provide a pharmacological agent to the patient,
wherein the processor is further configured to:
output feedback to the drug administration device so as to regulate administration of the pharmacological agent for a desired effect.

6. The physiological monitoring system of claim 1, wherein the processor is further configured to provide a control output to at least one of drug-infusion equipment or medical gas ventilation equipment based at least in part on the combined index indicative of both the level of pain and the depth of consciousness of the patient.

7. The physiological monitoring system of claim 1, wherein the processor is further configured to generate a displayable output including a visual indication of the combined index indicative of both the level of pain and the depth of consciousness of the patient.

8. The physiological monitoring system of claim 7, wherein the visual indication comprises at least one of a number, a color, or a graph.

\* \* \* \* \*